(12) United States Patent
Novelli et al.

(10) Patent No.: US 8,895,697 B2
(45) Date of Patent: Nov. 25, 2014

(54) ISOLATED MONOPHOSPHORYLATED PEPTIDE DERIVED FROM HUMAN ALPHA-ENOLASE USEFUL FOR DIAGNOSIS AND TREATMENT OF PANCREATIC ADENOCARCINOMA, ANTIBODIES DIRECTED AGAINST THE SAID MONOPHOSPHORYLATED PEPTIDE, AND USES THEREOF

(75) Inventors: Francesco Novelli, Turin (IT); Barbara Tomaino, Rivarolo Canavese (IT); Paola Cappello, Turin (IT)

(73) Assignee: Natimab Therapeutics S.r.l., Turin (IT)

( * ) Notice: Subject to any disclaimer, the term of this patent is extended or adjusted under 35 U.S.C. 154(b) by 138 days.

(21) Appl. No.: 13/394,350

(22) PCT Filed: Sep. 9, 2010

(86) PCT No.: PCT/IB2010/054069
§ 371 (c)(1),
(2), (4) Date: Mar. 6, 2012

(87) PCT Pub. No.: WO2011/030302
PCT Pub. Date: Mar. 17, 2011

(65) Prior Publication Data
US 2012/0164146 A1 Jun. 28, 2012

(30) Foreign Application Priority Data
Sep. 11, 2009 (IT) ............................... TO2009A0697

(51) Int. Cl.
C07K 7/00 (2006.01)
G01N 33/574 (2006.01)
C12N 9/88 (2006.01)

(52) U.S. Cl.
CPC ............ *C12N 9/88* (2013.01); *G01N 33/57438* (2013.01); *C12Y 402/01011* (2013.01)
USPC ........... 530/327; 530/324; 530/325; 530/326; 435/7.23

(58) Field of Classification Search
None
See application file for complete search history.

(56) References Cited

U.S. PATENT DOCUMENTS 7,745,391 B2 * 6/2010 Mintz et al. .................. 514/19.3

FOREIGN PATENT DOCUMENTS

WO 2008037792 4/2008

OTHER PUBLICATIONS

Ali et al., Influence of subculturing on gene expression in a *Theileria lestoquardi*-infected cell line, Vaccine 26S, G17-23 (Oct. 2008).
International Search Report of PCT/IB2010/054069, (Dec. 2010).
International Preliminary Report on Patentability of PCT/IB2010/054069, (Mar. 2012).
Written Opinion of PCT/IB2010/054069, (Mar. 2012).

* cited by examiner

*Primary Examiner* — Sheela J Huff
(74) *Attorney, Agent, or Firm* — Henry J. Cittone; Cittone & Chinta LLP

(57) ABSTRACT

An isolated peptide of 12-20 amino acids in length comprising the amino acid sequence SEQ ID NO:1, wherein the serine residue (S) at position 8 of SEQ ID NO:1 is phosphorylated, is provided. Also provided is a human monophosphorylated alpha-enolase isoform wherein the serine residue (S) at position 419 of the human alpha-enolase amino acid sequence (SEQ ID NO:2) is phosphorylated and in which other post-translational modifications may be present. Further provided are antibodies capable of specifically binding the peptide and/or the isoform of the invention. The peptide, the isoform and the antibodies of the invention may be used in the diagnosis and/or amelioration and/or treatment of pancreatic adenocarcinoma.

10 Claims, No Drawings

ND STATES (1) # ISOLATED MONOPHOSPHORYLATED PEPTIDE DERIVED FROM HUMAN ALPHA-ENOLASE USEFUL FOR DIAGNOSIS AND TREATMENT OF PANCREATIC ADENOCARCINOMA, ANTIBODIES DIRECTED AGAINST THE SAID MONOPHOSPHORYLATED PEPTIDE, AND USES THEREOF

CROSS-REFERENCE TO RELATED APPLICATIONS

This application is a National Phase Application of PCT International Application No. PCT/IB2010/054069, International Filing Date, 9 Sep. 2010, claiming priority to Italian Patent Application No. TO2009A000697, filed 11 Sep. 2009, both of which are hereby incorporated by reference in their entirety.

FIELD OF THE INVENTION

The present invention is in the field of the diagnosis and treatment of tumour pathologies and particularly pancreatic ductal adenocarcinoma, also designated as PDAC.

More specifically, the present invention relates to an isolated monophosphorylated peptide derived from human alpha-enolase and an antibody specifically directed against the same, useful in the diagnosis and/or treatment of pancreatic ductal adenocarcinoma. Moreover, the invention refers to a monophosphorylated isoform of human alpha-enolase comprising the above-mentioned monophosphorylated peptide.

BACKGROUND OF THE INVENTION

PDAC is the most frequent pancreatic carcinoma and is the fourth cause of death in United States and Europe. Most of the patients die within twelve months and the survival percentage at five years from diagnosis is 2%. Pancreatectomy remains the main treatment for PDAC, but the benefits thereof are restricted to 20% of the cases in which diagnosis was made at an early stage. Despite the improvements occurred in medical and surgical treatments, including the use of monoclonal antibodies, vaccines and chemotherapy, very few biomarkers are hitherto available for PDAC diagnosis and prognosis, which on top of that are poorly reliable. The most used serological PDAC biomarker is the sialylated antigen from the Lewis blood group CA19.9, which is mainly used for monitoring the response to therapy. This antigen can effectively be present at high concentrations even in the serum of patients with benign pancreatic diseases, such as chronic pancreatitis and biliary obstruction, which results in false positives. Furthermore, this antigen is not expressed in 5-10% of the population and therefore is not suitable to be used in all PDAC patients.

For these reasons, alternative biomarkers for diagnosing PDAC are under examination. Identifying a biomarker that is reliable and usable in a high percentage of patients would allow to decrease the use of invasive procedures, such as biopsy collections and histopathologic examinations. A biomarker with these features could also be used for identifying and assessing novel drug candidates for PDAC treatment.

Large-scale analysis for protein and RNA expression is among the recently used technologies for identifying potential PDAC biomarkers. In particular, proteomic technologies have been used to identify antigens capable of inducing an antibody response in PDAC patients. This has been done by analysing protein profiles separated by two-dimensional electrophoresis (2-DE), recognised by serum from PDAC patients and subsequently identified by mass spectrometry. By characterising the B cell repertoire against antigens specifically expressed by tumour cells (the so-called Immunoma of human cancer), it may be possible to define specific targets that are involved in tumour immuno-survey and immuno-editing and understand the mechanisms responsible for uncontrolled cell proliferation and metastases.

Certain authors suggested that immunotherapy may be a practicable approach for pancreatic cancer. Actually, PDAC-specific protein lists have been generated on the basis of their high expression at the RNA level (WO2004/055519), or on the basis of large-scale proteomic or serological-proteomic analyses, by using sera from PDAC patients. However, as far as the inventors know, none of these proteins has been concretely proven useful as a specific diagnostic reagent for PDAC.

In the International Patent Application WO 2008037792, the existence of six different phosphorylated human alpha-enolase isoforms (ENOA1-6) is reported and the use of one of these isoforms, phosphorylated at least in three positions, is claimed for PDAC diagnosis. The description of WO2008037792 shows experimental data concerning the analysis of the phosphorylation of the ENOA3 isoform, but this isoform is actually not related to PDAC. By contrast, the isoforms ENOA1 and ENOA2—related to PDAC—have not been sufficiently characterised in structural terms and no unequivocal criterion is provided in order to distinguish them from non-PDAC related isoforms.

Therefore, a need remains to detect and characterise a biomarker that is specific and reliable for early PDAC diagnosis, designed to distinguish this serious tumour pathology from other pathologies.

SUMMARY OF THE INVENTION

These and other objects are achieved by a monophosphorylated peptide isolated from alpha-enolase of 12 to 20 amino acids in length, characterised in that it comprises the amino acid sequence RIEEELGSKAKF (SEQ ID NO:1), and said peptide is phosphorylated only at the serine residue (S) at position 8 of SEQ ID NO:1.

Another aspect of the invention is a monophosphorylated human alpha-enolase isoform, characterised in that it comprises the amino acid sequence comprised between positions 2 and 434 of SEQ ID NO:2, the said isoform being phosphorylated only at the serine residue (S) at position 419 of SEQ ID NO:2.

SEQ ID NO:2 is the amino acid sequence of human alpha-enolase available in the Uni-ProtKB database with the accession number P06733.

SEQ ID NO:1 corresponds to amino acid positions from 412 to 423 of SEQ ID NO:2.

The serine residue at position 8 of SEQ ID NO:1 corresponds to the serine residue at position 419 of SEQ ID NO:2.

In the description that follows, the isolated peptide and the human alpha-enolase isoform that form the object of the present invention will be designated as "monophosphorylated peptide" and "monophosphorylated isoform", respectively.

A further aspect of the invention is an antibody capable of specifically binding the monophosphorylated peptide and/or monophosphorylated isoform of the invention.

Still another aspect of the invention is a kit for the diagnosis of pancreatic ductal adenocarcinoma (PDAC), comprising as a specific reagent a specifically PDAC-related protein molecule selected from the isolated monophosphorylated peptide of the invention, the monophosphorylated alpha-enolase isoform of the invention, and antibodies capable of specifically binding the monophosphorylated peptide and/or monophosphorylated isoform of the invention.

Still another aspect of the invention is an immunoassay method for PDAC diagnosis, comprising the steps of:
 a) contacting a biological sample (preferably serum or blood) from a patient suspected of being affected by pancreatic ductal adenocarcinoma with the peptide or the alpha-enolase isoform of the invention;
 b) detecting whether a specific immunological binding occurs between the peptide or the isoform and autoantibodies possibly present in the patient's biological sample; the occurrence of said specific immunological binding being indicative of pancreatic ductal adenocarcinoma.

A further aspect of the invention is a method for the amelioration or treatment of pancreatic ductal adenocarcinoma comprising administering to a subject the antibody capable of specifically binding the monophosphorylated peptide and/or monophosphorylated isoform of the invention.

Further features of the invention are defined in the appended claims that are an integral part of the description.

DETAILED DESCRIPTION OF THE INVENTION

The present invention is based on the observation, made by the present inventors through the mass spectrometry (MS) technique, that human alpha-enolase isoforms being phosphorylated only at the serine residue (S) at position 419 of SEQ ID NO:2 are selectively expressed in the tumoral pancreas as compared to the healthy pancreas.

Such a finding is surprising particularly considering the prior art WO2008037792, wherein it is taught that the human alpha-enolase isoforms ENOA1 and ENOA2, specifically related to pancreatic adenocarcinoma, are phosphorylated at least at 3 positions.

The present inventors have also verified that an isolated peptide, from 12 to 20 amino acids in length, derived from human alpha-enolase, comprising the amino acid sequence SEQ ID NO:1, only phosphorylated on the serine residue (S) at position 8 of SEQ ID NO:1, is specifically recognised by IgG-type autoantibodies present in the serum of patients affected by PDAC, but absent from sera of healthy individuals and sera of individuals affected by other pancreatic pathologies.

Altogether, these findings allowed the inventors to establish a fast and reliable in vitro immunoassay for PDAC diagnosis.

In the context of the present description, the term "diagnosis" means the identification of the pathology and/or the assessment of its progression, as well as, optionally, the evaluation of the patient's response to therapy by detecting autoantibodies designed to specifically recognise the monophosphorylated peptide and/or the monophosphorylated alpha-enolase isoform that form the object of the present invention.

The monophosphorylated peptide of the invention was synthesized in the solid phase and conjugated with a carrier through an additional cysteine residue at the amino-terminal position. To this end, any per se known peptide synthesis and conjugation technique may be used.

An illustrative and not limitative example of solid-phase synthesis of the monophosphorylated peptide of the invention and the conjugation thereof with chicken ovalbumin (OVA) as the carrier is provided in the following experimental section. The conjugation with the carrier allows for an easy anchorage to the solid support used for setting up the in vitro assay, while enabling the peptide to bend in space and be accessible for binding with antibodies. Non-limiting examples of carriers other than chicken ovalbumin are the following: bovine serum albumin (BSA), Keyhole-Limpet hemocyanine, *E. coli* maltose-binding protein, poly-arginine, poly-histidine, glutathione S-transferase, and the like.

As will be illustrated in more detail in the experimental section, the inventors synthesized two peptides, both consisting of the amino acid sequence CRIEEELGSKAKF (SEQ ID NO:3), one of which being phosphorylated only at the serine residue and the other being devoid of any phosphorylation whatsoever. The non-phosphorylated peptide SEQ ID NO:3 was used in order to assess the specificity of the reactivity of the antibodies against the monophosphorylated SEQ ID NO:3 peptide.

Both the monophosphorylated SEQ ID NO:3 peptide and the non-phosphorylated SEQ ID NO:3 peptide were conjugated with chicken ovalbumin (OVA) and immobilised onto microplates as the supports for carrying out the immunoassay. A person having ordinary skill in the art is capable of replacing the microplate with any solid support suitable for carrying out an immunoassay, such as for instance a polystyrene, silica or nitrocellulose support.

Sera from healthy subjects and patients affected by PDAC were preincubated with OVA, commercially available, for example, from Pierce (Rockford, Ill., USA), in order to eliminate the antibodies directed against the carrier, after which they were reacted with the monophosphorylated SEQ ID NO:3 peptide and the non-phosphorylated SEQ ID NO:3 peptide, both of them in the conjugated form with ovalbumin and immobilised on the microplate wells.

The presence of IgG autoantibodies capable of specifically recognising the monophosphorylated SEQ ID NO:3 peptide in the tested sera was detected with a horseradish peroxidase-conjugated rabbit anti-human IgG polyclonal antibody. A person having ordinary skill in the art is capable of replacing such a detection system with any alternative detection system suitable for use in an immunoassay, preferably an immunoenzymatic assay, such as for example an ELISA or EIA assay, or a radioimmunoassay (RIA).

Table 1 shows the results obtained in terms of reactivity of sera from healthy subjects (HS), PDAC patients and patients with tumours different from the pancreatic-derived ones (non-PDAC), towards the monophosphorylated SEQ ID NO:3 peptide and the non-phosphorylated SEQ ID NO:3 peptide.

TABLE 1

| Subjects | CRIEEELG(Sp)KAKF O.D. (x ± sem) | Frequency of subjects with OD > HS | CRIEEELGSKAKF O.D. (x ± sem) | Frequency of subjects with O.D. > HS |
|---|---|---|---|---|
| HS (n = 33) | 0.9 ± 0.06 | 0 | 1.35 ± 0.06 | 0 |
| PDAC (n = 122) | 1.42 ± 0.05 | 79 | 1.57 ± 0.04 | 52 |
| non-PDAC (n = 27) | 0.41 ± 0.03 | 0 | 0.44 ± 0.03 | 0 | x = mean;
sem = standard error of the mean

The presence of specific autoantibodies against the monophosphorylated SEQ ID NO:3 peptide in the tested sera was assessed in the PDAC patients and compared with the healthy subjects (HS) and the patients affected by non-pancreatic tumours (non-PDAC).

The presence of autoantibodies capable of binding the monophosphorylated SEQ ID NO:3 peptide was observed to be significantly higher in the PDAC sera than in sera from healthy subjects and sera from non-PDAC subjects. The percentage of PDAC patients that, exceeding the threshold of mean OD+standard error of healthy subjects (HS), was considered positive for the presence of specific antibodies anti-monophosphorylated SEQ ID NO:3 peptide reaches 79%.

The monophosphorylated SEQ ID NO:3 peptide was subjected to in silico analysis by using the Expasy search engine and phosphorylation was observed to be an event peculiar to PDAC, since it is non described in any other animal, plant or bacterial organism. Instead, the presence of self-antibodies capable of specifically recognising the non-phosphorylated SEQ ID NO:3 peptide resulted high both in the healthy donors and the PDAC patients and no significant differences were observed between the two groups, even though 52% of PDAC patients showed an OD higher that the threshold of OD+standard error of the mean of the healthy subjects.

The amino acid sequence SEQ ID NO:3 was inserted into Blast and aligned with all the sequences included in the database. The alignment showed that the 13 amino acids that make up this sequence not only are common to alpha-enolases from other species (for instance bacteria, mouse, rat), but to other proteins too, which explains the high reactivity of the sera against the non-phosphorylated SEQ ID NO:3 peptide.

The results obtained by the present inventors demonstrate that the monophosphorylated peptide of the invention is able to capture specific anti-monophosphorylated alpha-enolase autoantibodies which are present nearly in 80% of PDAC patients but absent from healthy subjects. This indicates that the monophosphorylated peptide of the invention is an effective diagnostic tool for human pancreatic adenocarcinoma.

As previously mentioned, a further object of the present invention is an antibody capable of specifically binding the monophosphorylated peptide of the invention.

In the context of the present description, the term antibody comprises both polyclonal antibodies and monoclonal antibodies. The term antibody also comprises whole immunoglobulins (preferably IgGs) or any fragment or derivative thereof having the same binding specificity as the whole immunoglobulin.

A monoclonal antibody can be obtained by any technique known per se, such as for instance the hybridoma technique or the technique of immortalising B lymphocytes, from patients with a high antibody titre, with Epstein Barr virus, which allows to obtain human monoclonal antibodies.

Since the monophosphorylated alpha-enolase isoform as previously defined comprises the monophosphorylated peptide of the invention within its own amino acid sequence, antibodies directed against the isolated monophosphorylated peptide are also likely to be able to bind the monophosphorylated isoform at the same amino acid sequence.

Such an antibody, specifically directed against the monophosphorylated peptide and also capable of recognising the monophosphorylated isoform of the invention, is particularly suitable for use as a specific diagnostic reagent, as it will be able to selectively bind to tissues expressing the human alpha-enolase isoforms related to PDAC. It will be possible to detect such a binding by any in vitro or in situ per se known detection technique. For a diagnostic detection, in situ detection is preferred, which does not imply the need of obtaining biopsies with invasive procedures. An in situ detection technique for example is the imaging technique, which comprises conjugating the antibody with a suitable detectable molecule, such as for instance a fluorescent dye.

When used for diagnosis, the protein molecule specifically related to PDAC (that is, the isolated monophosphorylated peptide, the monophosphorylated isoform of the invention and the antibody specifically directed against the same) is provided as a diagnostic kit. Besides the specific reagent, the diagnostic kit optionally comprises detection means and instructions for carrying out the diagnostic assay.

An antibody specifically directed against the monophosphorylated isoform of the invention is also suitable for use in the therapeutic treatment of PDAC, as the generation of a cytotoxic antibody (i.e. activating the antibody- or complement-dependent cytotoxicity) might mediate the selective elimination of PDAC cells that are characterised in that they express the α-enolase monophosphorylated isoform. Therefore, a pharmaceutical composition for the therapeutic treatment of PDAC, comprising a pharmaceutically effective amount of a monoclonal or polyclonal antibody specifically directed to the monophosphorylated isoform of the invention, and optional pharmaceutically acceptable carriers, excipients and/or diluents, falls within the scope of the present invention. The composition can be administered in (a) single or multiple dosage(s) and/or by using appropriate devices, through diverse administration routes such as for instance by intramuscular, intravenous, subcutaneous, topic, mucosal route, within non-biodegradable matrixes or by using appropriate drug release systems. In particular, the pharmaceutical composition of the invention is suitable for achieving administration of the active principle at the pancreas level or at any other tissue that may express the proteins specifically associated with PDAC.

The human monophosphorylated alpha-enolase isoform that forms the object of the present invention was isolated and characterised as described in the following experimental section.

Through the mass spectrometry technique, it has been possible to characterise such isoform with regard to post-translational modifications. Thus, it was seen that the human PDAC-related alpha-enolase isoforms (which in WO2008/037792 were designated as ENOA1 and ENOA2) share the following post-translational modification pattern:
  i) phosphorylation only at the serine residue at position 419 of SEQ ID NO:2;
  ii) acetylation on the lysine residue at position 420 of SEQ ID NO:2;
  iii) acetylation on the lysine residue at position 81 of SEQ ID NO:2;
  iv) methylation on the glutamic acid residue at position 88 of SEQ ID NO:2.

The elucidation of the post-translational modification pattern characteristic of these PDAC-related isoforms allows to distinguish them unequivocally from the remaining non-PDAC related isoforms, such as for example ENOA3.

The human monophosphorylated alpha-enolase isoform that forms the object of the invention is also suitable for use as the antigen in order to obtain monoclonal or polyclonal antibodies for therapeutic or diagnostic use for PDAC.

Such an isoform is further suitable for use in a screening assay to assess the reactivity of human anti-alpha-enolase antibodies as therapeutic or diagnostic tools for PDAC.

The following experimental section is provided solely by way of illustration and is not intended to limit in any way the scope of the present invention as defined in the appended claims.

EXPERIMENTAL SECTION

1) Peptide Synthesis

The phosphorylated and non-phosphorylated SEQ ID NO:3 peptides were prepared by the Fmoc solid phase peptide synthesis (SPPS) method, which comprises the successive addition of amino acids in order to create a linear peptide chain (Merrifield, R. B. (1963) Solid phase peptide synthesis. I. The synthesis of a tetrapeptide. J. Am. Chem. Soc. 85, 2149-2154; Carpino, L. A. & Han, G. Y. (1970) The 9-fluorenylmethoxycarbonyl function, a new base-sensitive amino-protecting group. J. Am. Chem. Soc. 92, 5748-5749). The chain C-terminus was covalently linked to a solid support, that is the HMP (4-hydroxymethylphenoxymethyl-RAPP-Polimer) resin. The amino acids were derivatised to prevent undesirable secondary reactions to occur and were protected on the alpha-$NH_2$ with the Fmoc group (9-fluorenylmethyl-carbonyl). During de-protection, the Fmoc group was removed with piperidine (Biosolve/Sigma), so as to allow the successive reaction to occur between the alpha-$NH_2$ group of the resin-bound peptide and the activated amino acid.

The synthesis was performed with an automated peptide synthesizer (Symphony, Protein Technologies). A synthesis scale of 25 μmoles was used, the amount by weight of amino acid in each cartridge was 75 μmoles.

Each amino acid was activated for 10 minutes with HBTU/HOBt 0.2 M in DMF and DIEA 0.4 M in DMF.

All the standard amino acids are commercially available and were purchased from AGTC Bioproducts, whereas the non-standard ones, such as for instance the phosphorylated amino acids (Ser, Tyr, Thr), were purchased from Iris Biotech or Novabiochem. In each step, dimethylformamide (DMF) was used as the solvent. De-protection (removal of the Fmoc group) was carried out in about 20 minutes with 20% piperidine in DMF. The conjugation time was 30 minutes.

Once the synthesis was complete, the bond between the resin and the peptide was ruptured by using a 95% trifluoroacetic acid (TFA)/2.5% $H_2O$/2.5% triisopropylsilane solution for at least 1.5 hours, with simultaneous removal of all the side chain protecting groups.

Finally, the free peptides were precipitated in diethyl ether. The volume of ether was 10 times the volume of TFA used for the rupture.

After detachment from the solid support, the isolated peptides were run in a C18 reverse-phase analytical HPLC column (Vydac) under the following conditions: C18; A=$H_2O$/0.3% B/0.1% TFA; B=50% Acetonitrile/50% $H_2O$/0.1% TFA; Gradient: from 95% A-5% B to 85% B in 30'.

Purification was carried out with a Shimadzu system for preparative HPLCs.

The purified peptides were conjugated with the chicken ovalbumin carrier protein by the cross-linker Sulfo-SMCC method (Tsao J L, Lin X, Lackland H, Tous G, Wu Y L, Stein S. (1991). Internally standardized amino acid analysis for determining peptide carrier protein coupling ratio. Anal. Biochem. 197:137-142). This method uses the cysteine sulfidrilic group (—SH) and is preferred over the conjugation according to the glutaraldehyde method wherein the peptide sequence contains other amino groups, such as for example the lysine side chains. In order to apply the Sulfo-SMCC method, it is important to have a cysteine at the C-terminus or N-terminus of the peptide sequence. This assures the selective conjugation of the carrier protein precisely onto the cysteine —SH group, to provide a 1:1 peptide/carrier conjugate.

Conjugation was performed by placing the preformed OVA (Pierce)+Sulfo-SMCC (Sigma) conjugate in PBS buffer (pH 7.4) with the peptide at room temperature for 4/5 hours. After which, the solution was subjected to dialysis on a cellulose membrane to eliminate the unreacted peptide and OVA. In the final step, the OVA-peptide conjugate was purified by gel-filtration on a Sephadex column (Amersham).

2) Enzyme-Linked ImmunoSorbent Assay (ELISA) for Detecting Specific Human IgGs Against the Monophosphorylated Peptide of the Invention EIA/RIA Stripwell™ microtiter plates (Costar Lifesciences, # cat. 2580, Acton, Mass., USA) were coated in triplicate with 50 μl of chicken ovalbumin-monophosphorylated peptide of the invention ("OVA-phosphopeptide") conjugate diluted in PBS 1×pH 7.3 at 1 μg/ml and were incubated overnight at room temperature (RT). The rows were washed 3 times with PBS and the unspecific binding sites were blocked with 200 μl/well of PBS containing 4% bovine serum albumin (Sigma, S. Louis, Mich., USA) for 1.5 hours at RT and washed 4 times with PBS 1× containing 0.05% Tween 20 (Scharlau Chemie SA, Barcelona, Spain) (PBS-Tween).

Concurrently, each serum diluted 1:100 was preincubated in a PBS-Tween solution containing 1% BSA and 2.5% chicken OVA (Sigma, cat. A5378) in 0.5-ml tubes (Eppendorf, Hamburg, Germany) for 30 minutes at 37° C. and then added (50 μl) to the coated row of wells for 2 hours at RT. After 8 washes with PBS-Tween, the rows were incubated with horseradish peroxidase (HRP)-conjugated rabbit anti-human IgG polyclonal antibody (Santa Cruz, Biotechnology Inc., Santa Cruz, Calif., USA) diluted in PBS-Tween containing 1% BSA for 1 hour at RT. After 6 washes with PBS-Tween and 2 washes with PBS 1×, the substrate Tetramethylbenzidine (TMB, BioFX Laboratories, Owings Mills, Md., USA) was added to the rows and allowed to develop the coloured reaction at RT. The reaction was stopped with 2N hydrochloric acid and the plates were read at 450 nm with a M550 Microplate Reader (BioRad, Segrate, Italy).

3) Purification of the Monophosphorylated Human Alpha-Enolase Isoform

A cell lysate from the pancreatic CF-PAC-1 line (ECACC ref. no. 91112501) was obtained by Tris HCl 50 mM, NaCl 150 mm, 1% NP40, 1 mM sodium orthovanadate, DTT 50 mM, protease inhibitor cocktail (PMSF 1 mM, Leupeptin, Pepstatin A, Aprotinin 10 μg/ml). The lysate was precipitated in acetone (1:5) and re-suspended in "PROTEIN OFFGEL stock solution" buffer (Agilent, Santa Clara, Calif., USA), separated by liquid isoelectrofocusing with 3100 Offgel fractionator (Agilent). The fractions containing the alpha-enolase were analysed by two-dimensional electrophoresis 2-DE followed by Western blot as previously described (Tomaino B et al., 2007). Five hundred μgs of protein were loaded onto 3 strips (GE Healthcare Amersham Biosciences) 13 cm long in order to obtain a better separation of the 6 ENOA isoforms. The 3 obtained two-dimensional gels were stained with the colloidal mass-compatible dye Coomassie Blue. The individual ENOA isoforms from the 3 gels were collected, pooled so as to increase the amount of total protein and subjected to mass spectrometry analysis to identify phosphorylated residues.

For the spectrometric analysis, the isoforms were de-stained, digested with trypsin according to known procedures (Shevchenko, A. et al., 1996). The peptides thus extracted were analysed by tandem nanospray mass spectrometry coupled with reverse phase liquid chromatography (LC-MS/MS) by using the mass spectrometer LTQ-Orbitrap (Thermo Fisher) (Luchini, A. et al., 2008). The reverse phase chromatographic column (LC) was packed with silica derivatised with 5 µm C18 chains with 200 Å pores (Michrom BioResources, CA, USA). After injection of the sample, the column was washed for 5 minutes with a mobile phase A (0.1% formic acid) and the peptides were eluted with a mobile phase B (0.1% formic acid, 80% acetonitrile) through a linear gradient from 0% to 45% in 120 minutes at a flow rate of 200 nl/minute and then at 100% phase B for 5 more minutes. The peptides were then ionized and analysed with the mass spectrometer LTQ-Orbitrap.

The MS ions are cumulated into the linear LTQ ion trap, isolated, fragmented (MS/MS) and subsequently sent to Orbitrap that analyses masses at an extremely high resolution. Analysis in databanks was carried out with the raw data. The peptide sequences derived from the MS/MS spectra were compared to the NCBI human databank by using the interface SEQUEST (Bioworks software, Thermo). The search was carried out so as to identify phosphorylations in Serine/Threonine/Tyrosine while considering the modifications caused by technical procedures such as alkylation of cysteines and oxidation of methionines. The results were filtered by choosing highly stringent criteria (mass accuracy not higher than 10 ppm). The spectra of the phosphorylated peptide candidates were then analysed manually in order to verify the effectiveness thereof.

The spectrum analysis enabled to identify a phosphopeptide within the ENOA isoforms 1 and 2, which shows, compared to the unmodified peptide, an increase in mass of 80 Da due to the presence of the single phosphate acquired. The peptide IEEELGS(p)KAK (amino acid positions 413-422 of SEQ ID NO:2) was detected both in the non-phosphorylated form and the phosphorylated form. This indicates the presence of a phosphorylation on the Serine at position 419.

Obviously, the principle of the finding being understood, the embodiments and the realization details may be varied compared to what has been described solely by way of illustration, and still remain within the scope of the invention as defined in the appended claims.

REFERENCES

WO 2004/055519
WO 2008/037792
Merrifield, R. B. (1963) Solid phase peptide synthesis. I. The synthesis of a tetrapeptide. J. Am. Chem. Soc. 85, 2149-2154
Carpino, L. A. & Han, G. Y. (1970) The 9-fluorenylmethoxycarbonyl function, a new base-sensitive amino-protecting group. J. Am. Chem. Soc. 92, 5748-5749
Tsao J L, Lin X, Lackland H, Tous G, Wu Y L, Stein S. (1991). Internally standardized amino acid analysis for determining peptide carrier protein coupling ratio. Anal. Biochem. 197:137-142
Tomaino B, Cappello P, Capello M, et al. Autoantibody Signature in Human Ductal Pancreatic Adenocarcinoma. J Proteome Res 2007; 6: 4025-31
Shevchenko, A., Jensen O. N., Podtelejnikov, A. C., Sagliocco, F., Wilm, M., Vorm, O., Mortensen, P., Shevchenko, A., Boucherie, H., and Mann, M. (1996) Proc Natl Acad Sci USA 93, 14440-14445
Luchini, A.; Geho, D. H.; Bishop, B.; Tran, D.; Xia, C.; Dufour, R. L.; Jones, C. D.; Espina, V.; Patanarut, A.; Zhou, W.; Ross, M. M.; Tessitore, A.; Petricoin, E. F.; Liotta, L. A. Smart hydrogel particles: Biomarker harvesting: One-step affinity purification, size exclusion, and protection against degradation. Nano Lett. 2008, 8 (1), 350-361)

The invention claimed is:

1. An isolated monophosphorylated peptide of 12 to 20 amino acids in length, comprising SEQ ID NO:1, wherein the serine residue (S) at position 8 of SEQ ID NO:1 is phosphorylated.

2. The peptide of claim 1, comprising a cysteine residue at the amino-terminal or carboxy-terminal position.

3. The peptide of claim 1, consisting of SEQ ID NO:1.

4. The peptide of claim 2, consisting of SEQ ID NO:3.

5. The peptide of claim 1, wherein said peptide is conjugated with a carrier.

6. The peptide of claim 5, wherein the carrier is selected from the group consisting of: chicken ovalbumin (OVA), bovine serum albumin (BSA), Keyhole-Limpet hemocyanine, *E. coli* maltose-binding protein, poly-arginine, poly-hystidine, and glutathione S-transferase.

7. A kit for the diagnosis of pancreatic ductal adenocarcinoma comprising the peptide of claim 1.

8. An immunoassay method for the in vitro diagnosis of pancreatic ductal adenocarcinoma, comprising the steps of:
   a) contacting a biological sample from a subject with the peptide of claim 1, and
   b) detecting whether immunological binding occurs between said peptide and autoantibodies in the biological sample of the subject;
the occurrence of said specific immunological binding being indicative of pancreatic ductal adenocarcinoma.

9. The method of claim 8, wherein the biological sample is serum or blood.

10. The method of claim 8, comprising an immunoenzymatic or radioimmunological assay method.

* * * * *

SEQUENCE LISTING

```
<160> NUMBER OF SEQ ID NOS: 3

<210> SEQ ID NO 1
<211> LENGTH: 12
<212> TYPE: PRT
<213> ORGANISM: Artificial
<220> FEATURE:
<223> OTHER INFORMATION: Isolated peptide derived from human alpha-
      enolase
<220> FEATURE:
<221> NAME/KEY: MOD_RES
<222> LOCATION: (8)..(8)
<223> OTHER INFORMATION: PHOSPHORYLATION

<400> SEQUENCE: 1

Arg Ile Glu Glu Glu Leu Gly Ser Lys Ala Lys Phe
1               5                   10

<210> SEQ ID NO 2
<211> LENGTH: 434
<212> TYPE: PRT
<213> ORGANISM: Homo sapiens

<400> SEQUENCE: 2

Met Ser Ile Leu Lys Ile His Ala Arg Glu Ile Phe Asp Ser Arg Gly
1               5                   10                  15

Asn Pro Thr Val Glu Val Asp Leu Phe Thr Ser Lys Gly Leu Phe Arg
            20                  25                  30

Ala Ala Val Pro Ser Gly Ala Ser Thr Gly Ile Tyr Glu Ala Leu Glu
        35                  40                  45
```

Leu Arg Asp Asn Asp Lys Thr Arg Tyr Met Gly Lys Gly Val Ser Lys
50                  55                  60

Ala Val Glu His Ile Asn Lys Thr Ile Ala Pro Ala Leu Val Ser Lys
65                  70                  75                  80

Lys Leu Asn Val Thr Glu Gln Glu Lys Ile Asp Lys Leu Met Ile Glu
                85                  90                  95

Met Asp Gly Thr Glu Asn Lys Ser Lys Phe Gly Ala Asn Ala Ile Leu
            100                 105                 110

Gly Val Ser Leu Ala Val Cys Lys Ala Gly Ala Val Glu Lys Gly Val
        115                 120                 125

Pro Leu Tyr Arg His Ile Ala Asp Leu Ala Gly Asn Ser Glu Val Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Ala
                165                 170                 175

Asn Phe Arg Glu Ala Met Arg Ile Gly Ala Glu Val Tyr His Asn Leu
            180                 185                 190

Lys Asn Val Ile Lys Glu Lys Tyr Gly Lys Asp Ala Thr Asn Val Gly
        195                 200                 205

Asp Glu Gly Gly Phe Ala Pro Asn Ile Leu Glu Asn Lys Glu Gly Leu
    210                 215                 220

Glu Leu Leu Lys Thr Ala Ile Gly Lys Ala Gly Tyr Thr Asp Lys Val
225                 230                 235                 240

Val Ile Gly Met Asp Val Ala Ala Ser Glu Phe Phe Arg Ser Gly Lys
                245                 250                 255

Tyr Asp Leu Asp Phe Lys Ser Pro Asp Asp Pro Ser Arg Tyr Ile Ser
            260                 265                 270

Pro Asp Gln Leu Ala Asp Leu Tyr Lys Ser Phe Ile Lys Asp Tyr Pro
        275                 280                 285

Val Val Ser Ile Glu Asp Pro Phe Asp Gln Asp Asp Trp Gly Ala Trp
    290                 295                 300

Gln Lys Phe Thr Ala Ser Ala Gly Ile Gln Val Val Gly Asp Asp Leu
305                 310                 315                 320

Thr Val Thr Asn Pro Lys Arg Ile Ala Lys Ala Val Asn Glu Lys Ser
                325                 330                 335

Cys Asn Cys Leu Leu Leu Lys Val Asn Gln Ile Gly Ser Val Thr Glu
            340                 345                 350

Ser Leu Gln Ala Cys Lys Leu Ala Gln Ala Asn Gly Trp Gly Val Met
        355                 360                 365

Val Ser His Arg Ser Gly Glu Thr Glu Asp Thr Phe Ile Ala Asp Leu
    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Leu Arg Ile Glu Glu Glu
                405                 410                 415

Leu Gly Ser Lys Ala Lys Phe Ala Gly Arg Asn Phe Arg Asn Pro Leu
            420                 425                 430

Ala Lys

<210> SEQ ID NO 3
<211> LENGTH: 13
<212> TYPE: PRT

-continued

```
<213> ORGANISM: Artificial
<220> FEATURE:
<223> OTHER INFORMATION: Isolated peptide derived from human alpha-
      enolase
<220> FEATURE:
<221> NAME/KEY: MOD_RES
<222> LOCATION: (9)..(9)
<223> OTHER INFORMATION: PHOSPHORYLATION

<400> SEQUENCE: 3

Cys Arg Ile Glu Glu Glu Leu Gly Ser Lys Ala Lys Phe
1               5                   10
```